United States Patent [19]

Gillonnier et al.

[11] Patent Number: 5,147,664
[45] Date of Patent: Sep. 15, 1992

[54] PROCESS FOR PREPARING AN AQUEOUS SOLUTION OF AN ALKALI METAL SALT OF METHIONINE

[75] Inventors: Claude Gillonnier, Neris-les-Bains; René Moisson, Montlucon, both of France

[73] Assignee: A.E.C. Societe de Chimie Organique et Biologique, France

[21] Appl. No.: 807,664

[22] Filed: Dec. 16, 1991

Related U.S. Application Data

[60] Continuation of Ser. No. 545,757, Jun. 29, 1990, abandoned, which is a continuation of Ser. No. 251,846, Oct. 3, 1988, abandoned, which is a division of Ser. No. 936,393, Dec. 1, 1986, abandoned.

[30] Foreign Application Priority Data

Dec. 3, 1985 [FR] France ............................... 85 17847

[51] Int. Cl.⁵ .............................................. A23K 1/00
[52] U.S. Cl. ....................................... 426/2; 426/623; 426/630; 426/656; 426/807
[58] Field of Search ................... 426/2, 623, 630, 656, 426/807

[56] References Cited

U.S. PATENT DOCUMENTS

| | | | |
|---|---|---|---|
| 4,243,814 | 1/1981 | Pascal et al. ........................ | 562/559 |
| 4,436,910 | 3/1984 | Kleemann ........................... | 562/557 |
| 4,459,423 | 7/1984 | Doya .................................. | 562/559 |
| 4,677,224 | 6/1987 | Commeyras et al. ............... | 562/575 |
| 4,705,689 | 10/1987 | Tanner et al. ..................... | 562/2 |

OTHER PUBLICATIONS

Ault "Technique & Experiments of Organic Chemistry" Allyn and Bacon Inc Publishers (1983) pp. 294–296.

*Primary Examiner*—R. B. Penland
*Attorney, Agent, or Firm*—Morgan & Finnegan

[57] ABSTRACT

An aqueous solution of an alkali metal salt of methionine, which can be used as an additive in feedstuffs, is made by hydrolysis of methionine amide with an alkali metal hydroxide.

1 Claim, No Drawings

PROCESS FOR PREPARING AN AQUEOUS SOLUTION OF AN ALKALI METAL SALT OF METHIONINE

This is a continuation of co-pending application Ser. No. 07/545,757, filed on Jun. 29, 1990, which is a continuation of application Ser. No. 07/251,846, filed Oct. 3, 1988, which is a divisional of application Ser. No. 06/936,393 filed Dec. 1, 1986, now abandoned.

The present invention relates to preparing an aqueous solution of an alkali metal salt of methionine which can be used as an additive in feedstuffs for livestock.

Methionine, which is an essential amino acid, is used at low doses, generally less than 1%, as an additive in feedstuffs. It is important to be able to produce a homogeneous dispersion of methionine in the feed and to be able to proportion the methionine accurately.

The use of methionine in crystallized solid form has disadvantages which make it difficult to handle and proportion.

The use of solutions enables a homogeneous dispersion to be produced at concentrations which can be readily monitored.

Since methionine is only slightly soluble in water, it cannot be used as such in aqueous solution on account of the considerable volume which would have to be handled. However, alkali metal salts of methionine have greater solubility in water, and can be used in sufficiently concentrated solutions to achieve the objective sought.

Solutions of alkali metal methioninate, especially sodium methioninate, can be prepared by dissolving methionine in an aqueous solution of an alkali metal hydroxide. However, this procedure is not economically advantageous since it is necessary to isolate the methionine beforehand, before dissolving it in a suitable medium.

It is also known, from French Patent Applications 2,499,560, 2,499,563, 2,499,564, 2,499,565 and 2,499,566, to prepare aqueous solutions of sodium methioninate by saponification of 5-($\beta$-methylmercaptoethyl)hydantoin with an excess of sodium cerbonate and/or sodium carbonate and/or lime. However, during the saponification, substantial amounts of sodium hydroxide and/or calcium carbonate are formed, and have to be removed by suitable treatments (concentration, precipitation, filtration, etc).

According to French Patent 2,372,797, it is known to prepare methionine from the corresponding aminonitrile by the action of hydroxide ions in the presence of a ketone, the reaction proceeding via the intermediate aminoamide. According to this process, the hydrolysis is performed in an aqueous medium containing an alkali metal hydroxide in close to the stoichiometric amount.

It has now been found that the 4-methylmercapto-2-aminobutyramide obtained as an intermediate can be hydrolysed by alkali metal hydroxides without the formation of undesirable by-products such as dipeptides. Solutions of alkali metal methioninate prepared in this way can be directly used in feedstuffs. They may have a concentration, expressed as methionine, of 30 to 60%, and preferably 40 to 45%, by weight, and are free from harmful by-products and inorganic salts.

The process of the invention may be effected by heating 4-methylmercapto-2-aminobutyramide, optionally prepared in situ by the process described in French Patent 2,372,797, in an autoclave in an aqueous solution of an alkali metal hydroxide at a temperature of between 100 and 200° C. for 5 to 10 minutes, and then, after degassing to remove the ammonia formed, cooling the solution obtained, which can be used directly as an additive for feedstuffs.

In general, the amount of alkali metal hydroxide used is between 0,9 and 1,1 mole per mole of amide introduced. Sodium hydroxide is preferably used as the alkali metal hydroxide.

The hydrolysis of the amide can be performed in a dilute medium, and the solution of alkali metal methioninate obtained then brought to the desired concentration of 30 to 60%, preferably 40 to 45%, by removal of water. Preferably, however, the hydrolysis is performed in such a way that the solution of methioninate is obtained directly at the desired concentration, thereby making it possible to avoid the expensive operation of concentrating the solution.

The solution of alkali metal methioninate, preferably sodium methioninate, obtained by the process of the invention is stable, especially down to temperatures which can be as low as $-15$ to $-30°$ C., depending on their concentration. Moreover, the biological properties of the solutions obtained are equivalent to those of solid methionine.

The examples which follow illustrate the invention.

EXAMPLE 1

1 mole of 3-methylmercaptopropionaldehyde (MMPA) and 20 mg of triethylamine are introduced into a 500-cm$^3$ reactor in which it is possible to work under pressure.

1.05 mole of hydrocyanic acid is introduced at a temperature in the region of 20° C. After 10 minutes' reaction, 5 moles of liquid ammonia are added. The mixture is heated to 60° C. for 30 minutes under a pressure of 11.5 bars with vigorous agitation. On releasing the pressure, the excess ammonia is removed. The reaction mixture contains approximately 0.8 mole of residual ammonia per mole of aminonitrile formed. After the mixture has been cooled to a temperature in the region of 10° C., 350 g of an aqueous solution containing 0.2 mole of acetone and 0.2 mole of sodium hydroxide are introduced. The temperature rises to 20°-25° C. The mixture is heated to 30° C. for 1 hour. The excess ammonia and acetone are removed under reduced pressure. 68 g of 50% caustic soda solution (0.85 mole) are then added and the mixture is heated to 180° C. for 5 minutes. The pressure is 19 bars. The pressure is then reduced to atmospheric pressure, and the temperature falls to about 95° C. After the mixture has cooled to a temperature in the region of 20° C., 333 g of a yellow solution containing 43.4-0% by weight of methionine and 0.055% by weight of ammonia are obtained.

The yield of methionine is 37% with respect to the MMPA introduced.

The residual ammonia content can be reduced by concentration under reduced pressure.

Under these conditions, a solution is obtained whose characteristics are as follows:

| | |
|---|---|
| methionine | 43.7% by weight |
| | (0.293 mole/100 g) |
| Na | 7.08% (0.308 gram-atom/100 g) |
| ammonia | 0.013% |
| viscosity | 10 centistokes at 30° C. |
| density | 1.195 |

-continued

| | |
|---|---|
| crystallization point | −23° C. |

The following by-products are assayed by thin layer chromatography:

| | |
|---|---|
| diketopiperazine | less than 0.01% |
| hydantoin | less than 0.01% |
| hydantoic acid | less than 0.01% |
| ureidobutyramide | less than 0.01% |
| 2,4-diaminobutyric acid | 0.5 to 0.6% |
| 3-aminopyrrolidone | less than or equal to 0.01% |
| hexahydropyrimidine-carboxylic acid | less than or equal to 0.02% |
| methionine amide | 0.02% |
| L,L-dipeptide | 0.1% |
| D,L-dipeptide | 0,1% |

EXAMPLE 2

50 g of water, 88.8 g of 4-methylmercapto-2-aminobutyramide (0.60 mole) and 50.4 g of 50% sodium hydroxide solution (0.63 mole) are introduced into a 500-cm³ reactor in which it is possible to work under pressure. The mixture is completed by adding water so as to obtain a reaction mixture weighing 220 g. The mixture is heated to 120° C. in the course of 10 minutes, and then maintained at this temperature for 20 minutes with agitation. The ammonia formed is removed on releasing the pressure. The temperature falls to about 95° C. After the mixture has cooled to a temperature in the region of 20° C., 205 g of a pale yellow solution containing 43.2% by weight of methionine are obtained.

The yield is in the region of 99%.

The biological efficiency of the solutions of alkali metal methioninate obtained by the process of the present invention is comparable to that of the methionine customarily used in solid form, as shown by trials showing the effects of these products on the growth of chicks.

The trial is carried out on male chicks for a period of 8 to 28 days. The animals receive one of ten experimental diets derived from the same basic diet containing 0.54% of sulphur-containing amino acids, the composition of which is as follows:

| | |
|---|---|
| maize | 31% |
| maize starch | 28% |
| soya bean oil cake | 24% |
| gelatin | 10% |
| tallow | 3% |
| mineral salts and vitamins | 4% |
| L-lysine hydrochloride | 0.04% |
| L-tryptophan | 0.04% |
| D,L-isoleucine | 0.05% |
| D,L-leucine | 0.08% |
| crude proteins | 23.2% |
| lysine | 1.18% |
| methionine | 0.30% |
| methionine + cysteine | 0.54% |
| metabolizable energy | 3190 kcal/kg |

The experimental feedstuffs vary only in respect of the extent of addition of methionine (0; 0.05; 0.10 and 0.25%) and also in respect of the source of this supplementation (solid methionine containing 99% of methionine base, solution of sodium methioninate according to Example 1 assaying 43.7% of methionine base).

Each batch consists of 12 replicates of 6 chicks per cage.

The results are collated in Table I.

TABLE I

| SOURCE OF METHIONINE | EXTENT OF SUPPLEMENTATION % (BASE) | CONSUMPTION kg/ANIMAL | WEIGHT GAIN g/ANIMAL | FOOD CONVERSION |
|---|---|---|---|---|
| basic diet | 0 | 1.160 | 609 | 1.91 |
| D,L-methionine | 0.047 | 1.179 | 627 | 1.88 |
| Sodium D,L-methioninate according to Example 1 | 0.064 | 1.228 | 664 | 1.85 |
| Solid D,L-methionine | 0.097 | 1.237 | 684 | 1.81 |
| Sodium D,L-methioninate according to Example 1 | 0.102 | 1.234 | 694 | 1.78 |
| Solid D,L-methionine | 0.235 | 1.251 | 740 | 1.69 |
| Sodium D,L-methioninate according to Example 1 | 0.228 | 1.254 | 751 | 1.67 |

In Table II, the results are collated which show the variation in weight gain in terms of the source and the level of methionine consumed.

TABLE II

| REGRESSION EQUATION Y + ax + b | NUMBER OF POINTS PER LINE | CORRELATION COEFFICIENT | MOLECULAR EFFICIENCY |
|---|---|---|---|
| Solid D,L-methionine Y = 0.083 x + 586 | 36 | 0.74 | 100 |
| Sodium D,L-methioninate according to Example 1 Y = 0.086 x + 591 | 36 | 0.78 | 104 |

The comparison of the regression coefficients shows that the biological efficiency is the same for both the products in question.

We claim:

1. Method of supplying livestock with their dietary requirements of methionine which consists essentially of feeding to said livestock an amount effective to provide said dietary requirements of a stable solution of sodium methioninate free from inorganic salts and having a methionine content of 30 to 60% obtained by hydrolysing 4-methylmercapto-2-amino-butyramide with sodium hydroxide and removing the ammonia formed to produce a solution of sodium methioninate useful as such for directly feeding livestock.

* * * * *